(12) United States Patent
Hsu et al.

(10) Patent No.: US 8,524,168 B2
(45) Date of Patent: Sep. 3, 2013

(54) HOLDING DEVICE FOR MEDICAL TEST STRIP

(75) Inventors: Ming-Chang Hsu, Hsinchu (TW); Mon Wen Yang, Hsinchu (TW); Ming-Hsin Chuang, Taishan Township (TW); Thomas Y. S. Shen, Hsinchu (TW)

(73) Assignee: Apex Biotechnology Corp., Hsinchu Science-Based Industrial Park, Hsinchu (TW)

( * ) Notice: Subject to any disclaimer, the term of this patent is extended or adjusted under 35 U.S.C. 154(b) by 259 days.

(21) Appl. No.: 12/816,281

(22) Filed: Jun. 15, 2010

(65) Prior Publication Data
US 2010/0319170 A1 Dec. 23, 2010

(30) Foreign Application Priority Data
Jun. 19, 2009 (TW) ............................... 98211087 U

(51) Int. Cl.
*G01N 33/00* (2006.01)
(52) U.S. Cl.
USPC .............. 422/402; 422/50; 422/63; 422/68.1; 422/560; 422/561
(58) Field of Classification Search
USPC ...................... 422/402, 50, 63, 68.1, 560, 561
See application file for complete search history.

(56) References Cited

U.S. PATENT DOCUMENTS

| 7,449,148 B2 | 11/2008 | Matsumoto et al. |
| 2005/0145491 A1 | 7/2005 | Amano et al. |
| 2008/0217354 A1 | 9/2008 | Newman et al. |

FOREIGN PATENT DOCUMENTS

| EP | 1494021 A1 | 1/2005 |
| EP | 2071326 A1 | 6/2009 |

OTHER PUBLICATIONS

Extended European Search Report, EP Application No. 10166620.4, dated Jun. 15, 2011.

*Primary Examiner* — Sam P Siefke
(74) *Attorney, Agent, or Firm* — Snell & Wilmer L.L.P.

(57) ABSTRACT

A device for holding a medical test strip is provided. The device comprises a receiving casing having an opening for receiving the medical test strip and a first stopping portion protruding from an upper surface of the receiving casing; an ejection base having a cover and a pusher beneath the cover, the cover downwardly extending a second stopping portion for sliding against the upper surface of the receiving casing; and an elastic member located between the receiving casing and the ejection base. When the pusher moves toward the opening by an external force to eject the test strip from the opening, the elastic member is compressed and the second stopping portion slides away from the first stopping portion. When the external force disappears, the second stopping portion slides toward the first stopping portion by a resilient force of the elastic member until the first stopping portion and the second stopping portion are engaged.

13 Claims, 6 Drawing Sheets

HOLDING DEVICE FOR MEDICAL TEST STRIP

CROSS REFERENCE TO RELATED APPLICATIONS

This application claims the right of priority based on Taiwan Patent Application No. 98211087 entitled "HOLDING DEVICE FOR MEDICAL TEST STRIP," filed on Jun. 19, 2009, which is incorporated herein by reference and assigned to the assignee herein.

FIELD OF THE INVENTION

The present invention relates to a holding device for carrying a medical test strip, and in particular to a holding device in which a medical test strip is ejected without the need of touching the medical test strip in hands.

BACKGROUND OF THE INVENTION

Global aging population has resulted in a significant shortage of nursing resources. In order to reduce the pressure from social medical errors, improving the quality of home health care for illness recovery has long been one of the goals in the development of countries and industries. Accordingly, the in vitro diagnostic (IVD) industry is fast glowing. An estimate on the annual increasing rate of IVD demand is around 11.12% since 2002, in which the low-invasion IVD system is most acceptable for the users. However, even for the low-invasion IVD system, there is a need to sample a small amount of blood. Therefore, there exists a risk of infection for those who need to collect the test strips having blood because they have to touch the test strips in hands.

In addressing to this problem, Taiwan Patent No. I274158 provides an IVD apparatus 10 having a strip eject function as shown in FIG. 1. The IVD apparatus 10 is formed with a linked member 110, a pushing member 120 and a base 130. The linked member 110 includes a spring 111, a pick element 112 and a through hole 113. A test strip (not-shown) can be placed on a top plate of the pushing member 120. The pushing member 120 is further formed with a guiding shaft 121 to be engaged with the through hole 113 of the linked member 110. Specifically, when an external force plucks the pick element 112 and then move the pushing member 120 forward, the spring 111 is compressed and the test strip (not-shown) on the pushing member 120 is ejected out of the apparatus 10. When the pick element 112 is released, the resilience force of the spring 111 forces the pushing member 120 to return to its original position, and thus the pushing member 120 is received in the base 130. Although such apparatus may provide an ejection function to resolve the problem as aforementioned, they simultaneously bring lots of other problems due to its uneven resilience force, which results in a loose structure and being easy to get stuck of the test strip in use.

SUMMARY OF THE INVENTION

In order to obviate the previously mentioned problems, one aspect of the present invention provides a holding device by which a medical test strip can be ejected without the need of touching the medical test strip with hands. Based on one of the features of the present invention, the holding device can be operated smoothly as it generates less uneven stresses. Therefore, the structure of the holding device is not as loose as those of the prior art, and the problem of getting struck is also eliminated.

One of the features of the present invention is to provide a structure with stopping portions and/or guiding tracks such that the ejection action is proceeding smoothly with no significant vibrations caused by the excess and/or uneven resilience force.

In a first embodiment, the present invention provides a device for holding a medical test strip, the device comprising: a receiving casing having an opening for receiving the medical test strip and a first stopping portion protruding from an upper surface of the receiving casing; an ejection base having a cover and a pusher beneath the cover, the cover downwardly extending a second stopping portion for sliding against the upper surface of the receiving casing and selectively engaging with the first stopping portion; and an elastic member located between the receiving casing and the ejection base, wherein when the pusher moves toward the opening by an external force to eject the medical test strip from the opening, the elastic member is compressed and the second stopping portion slides away from the first stopping portion; and when the external force disappears, the second stopping portion slides toward the first stopping portion by a resilient force of the elastic member until the first stopping portion and the second stopping portion are engaged.

In a second embodiment, the present invention provides a device for holding a medical test strip, the device comprising: a receiving casing having an opening for receiving the medical test strip, a first stopping portion and a guiding portion protruding from an upper surface of the receiving casing, the first stopping portion is arranged perpendicular to the guiding portion; an ejection base having a cover and a pusher beneath the cover, the cover downwardly extending a second stopping portion arranged perpendicular to the guiding portion, the second stopping portion having a guiding groove movably engaged with the guiding portion so as to lead the second stopping portion sliding against the upper surface of the receiving casing; and an elastic member located between the receiving casing and the ejection base, wherein when the pusher moves toward the opening by an external force to eject the medical test strip from the opening, the elastic member is compressed and the second stopping portion slides away from the first stopping portion; and when the external force disappears, the second stopping portion slides toward the first stopping portion by a resilient force of the elastic member until the first stopping portion and the second stopping portion are engaged.

In a third embodiment, the present invention provides a device according to the second embodiment, wherein the receiving casing further comprises at least one guiding track; the elastic member further comprises at least one spring placed in the guiding track; and the ejection base further comprises at least one thrusting portion downwardly extended from the cover, wherein, when the pusher moves toward the opening, the thrusting portion enters the guiding track to compress the spring. In another embodiment, the receiving casing comprises two guiding tracks arranged on opposite sides of the receiving casing; the elastic member comprises two springs respectively placed in the two guiding tracks; and the ejection base comprises two thrusting portions downwardly extended from the cover and respectively corresponding to the two guiding tracks, wherein, when the pusher moves toward the opening, the two thrusting portions respectively enter the corresponding guiding tracks to compress the corresponding springs. According to these embodiments, there provides an ejection mechanism including the pusher corresponding to the opening, the guiding groove corresponding to the guiding portion, and the spring together with the thrusting portion corresponding to the guiding track. The holding device with such ejection mechanism can be operated smoothly as it generates even stresses during operation.

Another aspect of the present invention is to provide a feature of fastening used for avoiding the device structure being loosed by the excess resilient force. In a fourth embodiment, the present invention provides a device according to the first, second or third embodiment, further comprising at least one fastener having a vertical plane inserted into the receiving casing and a horizontal plane in connection with an external component. The fastener is preferably an L-shaped member. In another embodiment, two fasteners are respectively arranged on opposite sides of the holding device.

The invention still includes other aspects to resolve other problems, some of which are described in detail together with the abovementioned aspects in the following detailed description.

DETAILED DESCRIPTION OF THE INVENTION

Figure 1:
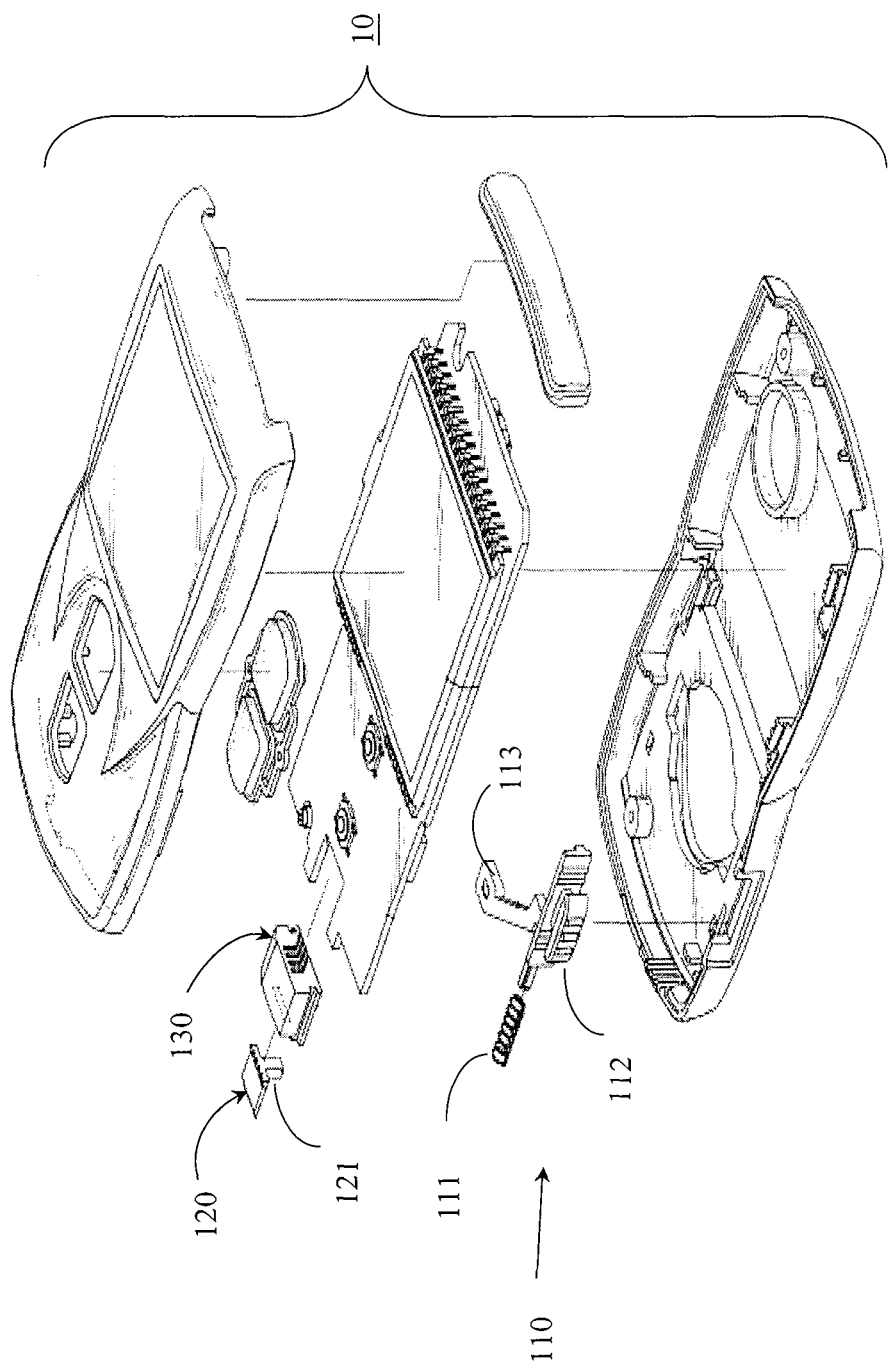
FIG. 1 illustrates a conventional in vitro diagnostic (IVD) apparatus.

The present invention may best be understood by reference to the following description in conjunction with the accompanying drawings, in which similar reference numerals represent similar elements. Any devices, components, materials, and steps described in the embodiments are only for illustration and not intended to limit the scope of the present invention. It should be noted that the features illustrated in the drawings are not necessarily drawn to scale. Descriptions of well-known components, materials, and process techniques are omitted so as not to unnecessarily obscure the embodiments of the invention.

Figure 2:
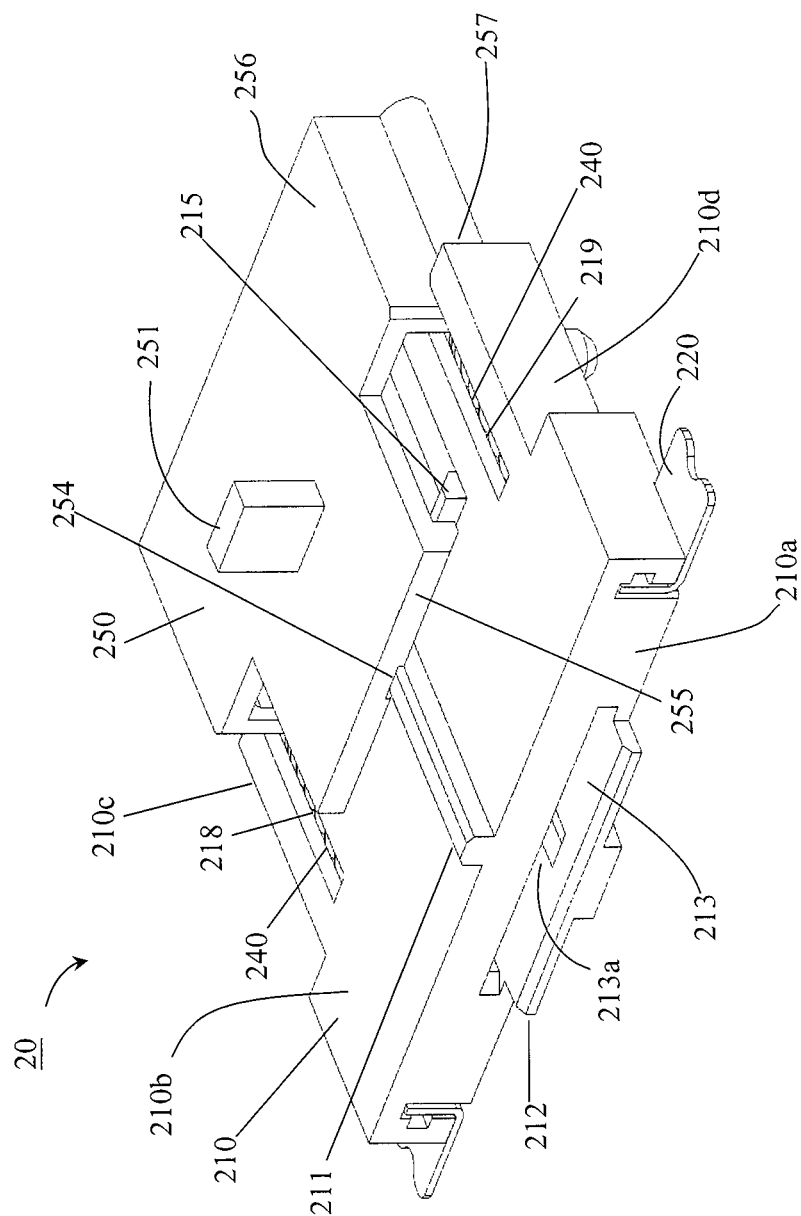
FIG. 2 illustrates a perspective view of a holding device in accordance with one embodiment of the present invention.
Figure 3:
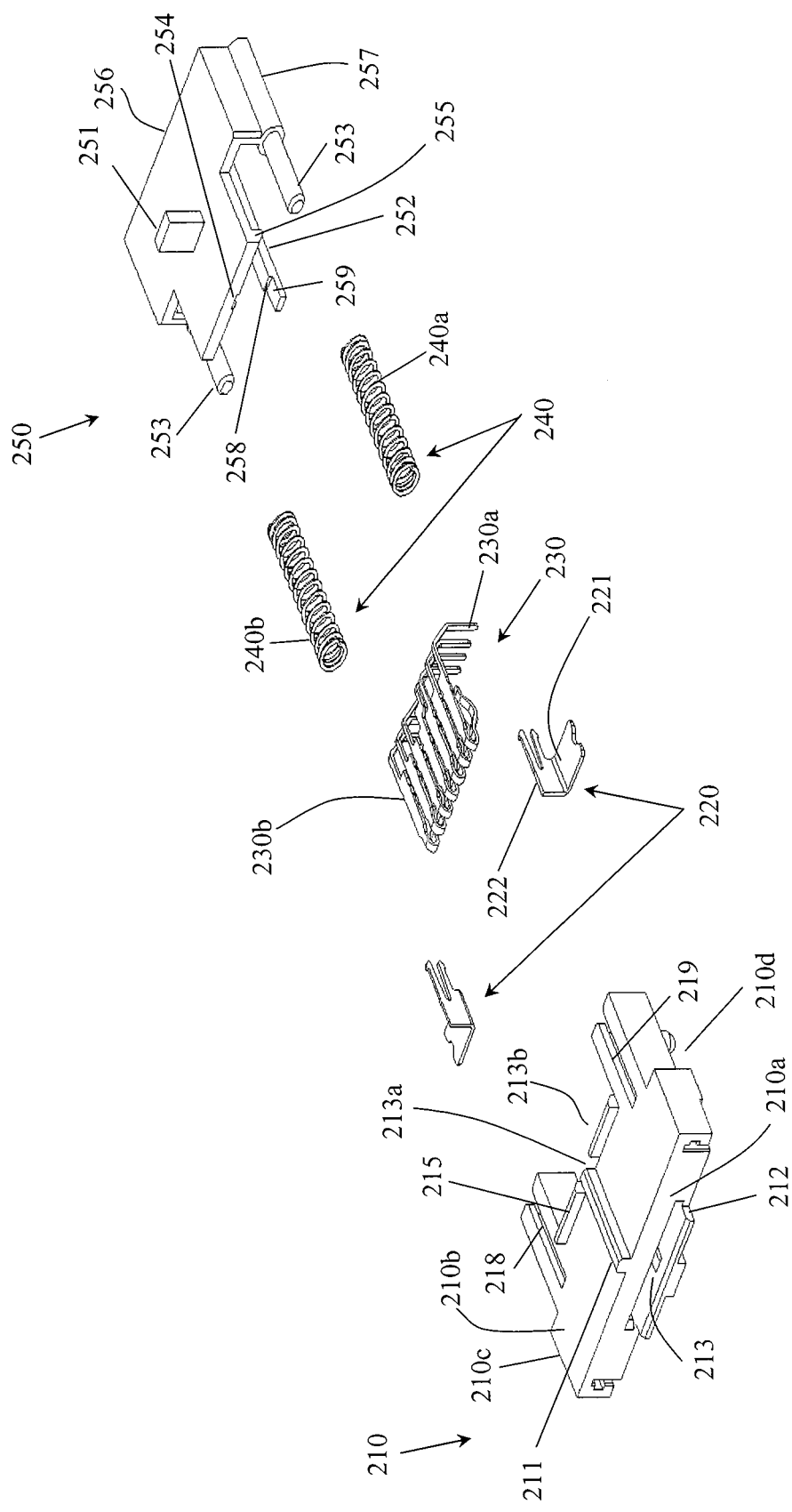
FIG. 3 illustrates an explosive view of the holding device of FIG. 2.

FIG. 2 illustrates a perspective view of a holding device 20 in accordance with one embodiment of the present invention. FIG. 3 illustrates an explosive view of the holding device 20 of FIG. 2. As shown in these figures, the holding device 20 includes a receiving casing 210, an ejection base 250, and an elastic member 240 located between the recovering casing 210 and the ejection base 250. The receiving casing 210 is formed with a tray 212 for holding a medical test strip (shown in FIG. 4 and FIG. 5). The receiving casing 210 also includes an opening 213 on a sidewall 210a of the receiving casing 210. The opening 213 communicates with an internal space 213a in which the tray 212 and other desired components, for example, sensing terminals are located. The receiving casing 210 is profiled with a concave 213b. The medical test strip is placed on the tray 212 within the internal space 213a via the opening 213. The concave 213b exposes a part of the internal space 213a. A guiding portion 211 and a first stopping portion 215 are projected form the upper surface 210b of the receiving casing 210. The guiding portion 211 and the first stopping portion 215, both in bar shapes, are arranged perpendicular to each other. A first guiding track 218 and a second guiding track 219 are respectively located on the opposite sides 210c and 210d in parallel. The concave 213b is between the guiding tracks 218 and 219.

As shown in FIGS. 2 and 3, the ejection base 250 includes a cover 256, an activated member 251 on and above the cover 256, a pusher 252 on and beneath the cover 256. The cover 256 is placed above the receiving casing 210 to shelter the concave 213b. The cover 256 extends downwardly a second stopping portion 255 and a thrusting portion 257. The thrusting portion 257 is used for pushing the elastic member 240. The thrusting portion 257 further horizontally extends a linked shaft 253. The activated member 251 may connect an external component, for example, an IVD apparatus (not shown). The second stopping portion 255 is selectively engaged with the first stopping portion 215 of the receiving casing 210. This will be specifically described hereafter. The second stopping portion 255 is formed with a guiding groove 254 movably engaged with the guiding portion 211 of the receiving casing 210. This provides a railway to guide the second stopping portion 211 to slide on the upper surface 210b of the receiving casing 210. Note that in other embodiments of the present invention, the guiding portion 211 and the first stopping portion 215 can be set on any suitable place only if they are respectively corresponding to the guiding groove 254 and the second stopping portion 255. For example, they can be set on near an edge of the receiving casing 210. The pusher 252 is used for pushing the medical test strip to leave away from the holding device 20. The pusher 252 is profiled with a step structure, which includes a first step with a horizontal surface 259 for supporting the medical test strip; and a second step having a vertical surface 258 to be against an edge of the medical test strip. The step structure is also shown on FIGS. 4 and 5.

Still referring to FIGS. 2 and 3, the elastic member 240 includes components made of elastic materials, preferably having spring but not limited thereto. In FIG. 3 of the embodiment, the elastic member 240 includes two springs 240a and 240b. The spring 240a/240b has one end in connection with the thrusting portion 257 of the ejection base 250 and another end in connection with the receiving casing 210. The linked shaft 253 is inserted into the spring 240a/240b. The springs 240a and 240b are respectively within the first guiding track 218 and the second guiding track 219 on the opposite sides of the receiving casing 210. In another preferred embodiment, the size of the guiding track 218/219 is substantially the same as the size of the spring 240a/240b. The term, "substantially the same" means that the spring 240a/240b is fitted into the guiding track 218/219. Such structure allows the elastic member 240 to generate even resilient force so as to have a smooth and steady ejection action.

As shown in FIG. 3, the holding device 20 further includes a plurality of sensing terminals 230 within the internal space 213a. The terminal 230 is formed with an electric pin 230a and a resilient portion 230b. The resilient portion 230b extends to connect with the tray 212. When the medical test strip is placed on the tray 212, it compresses the resilient portion 230b to create a starting electric signal. The electric pin 230a protrudes out of the receiving casing 210 and in connection with an external device, for example, the electric system of an IVD apparatus. The sensing terminals 230 and the electrodes of the medical test strip correspond with each other. Information regarding the sensing terminals 230 and the electrodes of the medical test strip is well known and described in, for example, Taiwan Patent Application No. 97208206, which is incorporated herein by reference.

Still referring to FIG. 2 and FIG. 3, the holding device 20 further includes a fastening component set 220. In the embodiment, the fastening component set 220 includes two L-shaped fasteners, respectively located on the opposite sidewalls 210c and 210d of the receiving casing 210 in parallel. By way of the fasteners, the holding device 20 can be fixed on an external device, for example the IVD apparatus. The L-shaped fastener is formed with a vertical plane 222 inserted into the receiving casing 210 and a horizontal plane in connection with the external device. The parts for fastening includes tenons or screws, but not limited hereto. The shape of fastener can be any other than the L-type.

Figure 4:
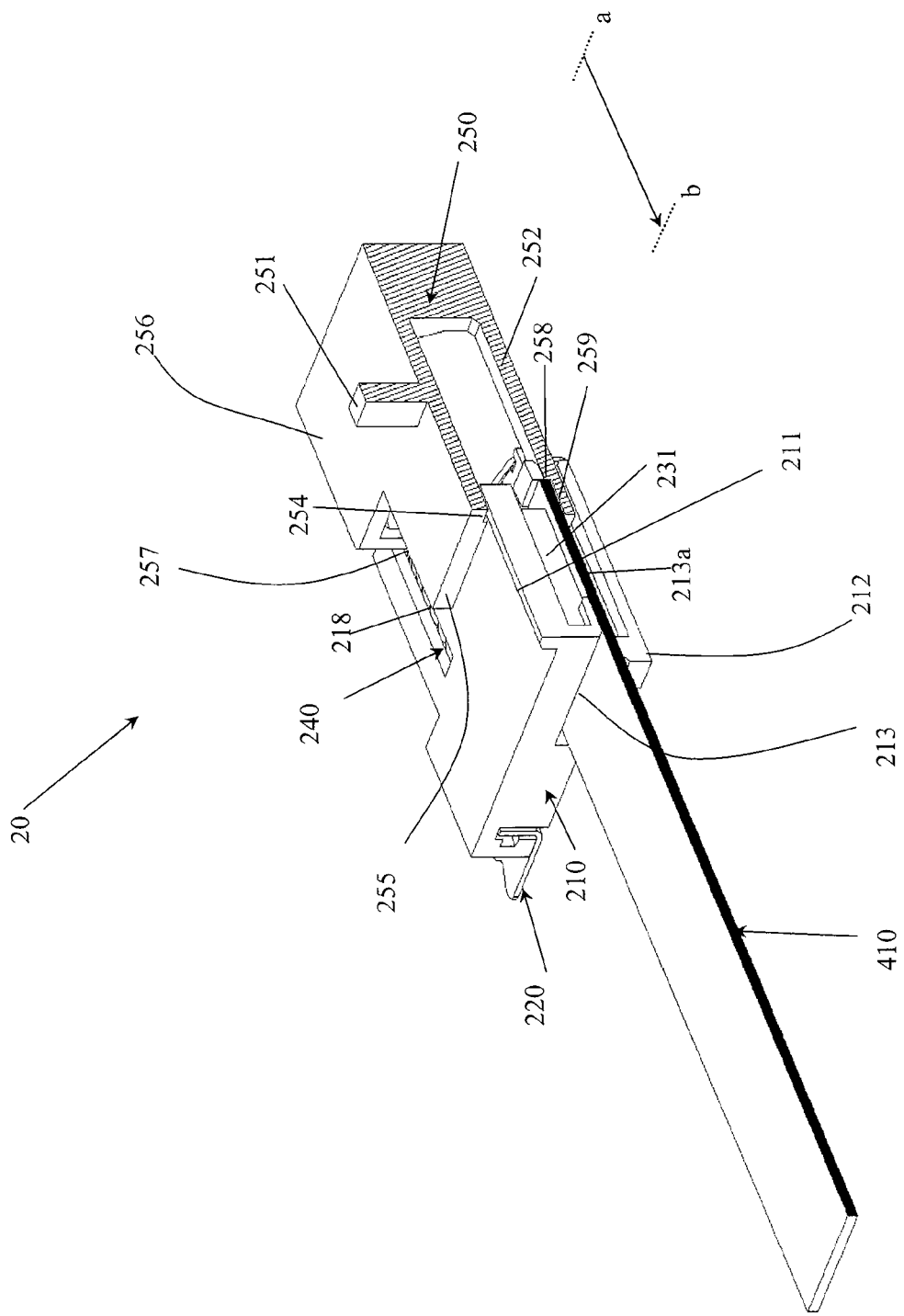
FIG. 4 illustrates a perspective view along one cross-sectional plane of a holding device in accordance with one embodiment of the present invention, wherein an elastic member is not compressed yet.
Figure 5:
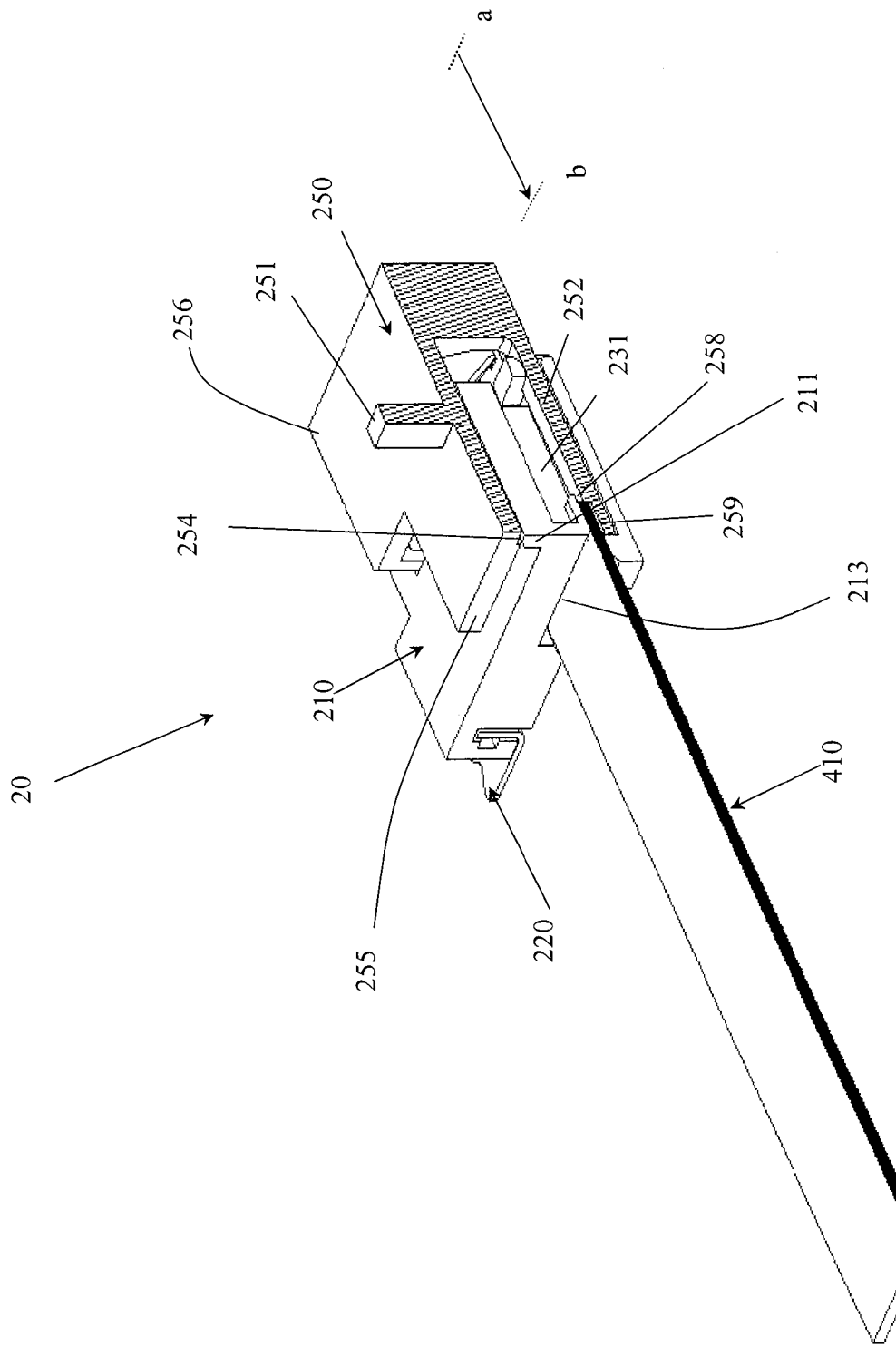
FIG. 5 illustrates a perspective view along one cross-sectional plane of a holding device in accordance with one embodiment of the present invention, wherein an elastic member is being compressed.

FIG. 4 illustrates a perspective view along one cross-sectional plane of the holding device 20 wherein the elastic member 240 is not compressed yet. FIG. 5 illustrates another perspective view when the elastic member 240 is being compressed. In addition to the medical test strip 410, all the elements of FIGS. 4 and 5 are the same with those in FIGS. 2 and 3, and thus they are represented with similar reference numerals hereinafter. As shown in FIG. 4, the holding device 20 includes the receiving casing 210, the ejection base 250 and the elastic member 240 not being compressed yet between the receiving casing 210 and the ejection base 250. The receiving casing 210 includes the tray 212, the opening 213, the guiding portion 211, the internal space 213a, and the first guiding track 218. The ejection base 250 includes the cover 256, the activated member 251, the pusher 252, the second stopping portion 255, and the guiding groove 254. The elastic member 240 includes two springs (only one being shown), respectively placed within the guiding tracks 218 and 219 and in connection with the thrusting portion 257. The pusher 252 includes the first step with the horizontal surface 259 for supporting the medical test strip 410; and the second step having the vertical surface 258 to be against by an edge of the medical test strip 410. In this embodiment, the height of the vertical 258 is lower than the thickness of the medical test strip 410. In another embodiment, the height of the vertical 258 may be greater than the thickness of the medical test strip 410.

Note that in FIG. 4, the holding device 20 is in the situation that the elastic member 240 is not compressed yet, and thus the ejection base 250 is located along the line a (i.e. the first placement). FIG. 5 illustrates the holding device 20 in the situation that the elastic member 260 is being compressed, and thus the ejection base 250 is located along the line b (i.e. the second placement). Specifically, when a user applies an external force on the IVD apparatus to move the activated member 251, the cover 256 is moved to force the pusher 252 to go toward the opening 213 and thus push the medical test strip 410 out of the opening 213. At the same time, the elastic member 240 is compressed so that the second stopping portion 255 is sliding away the first stopping portion 215, as shown in FIG. 5. Note that in FIG. 5, it illustrates the medical test strip 410 hanging on. In practice, in the situation of the second placement, the medical test strip 410 may have been ejected out of the receiving casing 210. When the external force disappears, the second stopping portion 255 slides toward the first stopping portion 215 by a resilient force of the elastic member 240 until the first stopping portion 215 and the second stopping portion 255 are engaged. When they are engaged, the ejection base 215 returns to the first placement (i.e. being located along the line a, as shown in FIG. 5, or FIG. 2 or FIG. 6).

Figure 6:
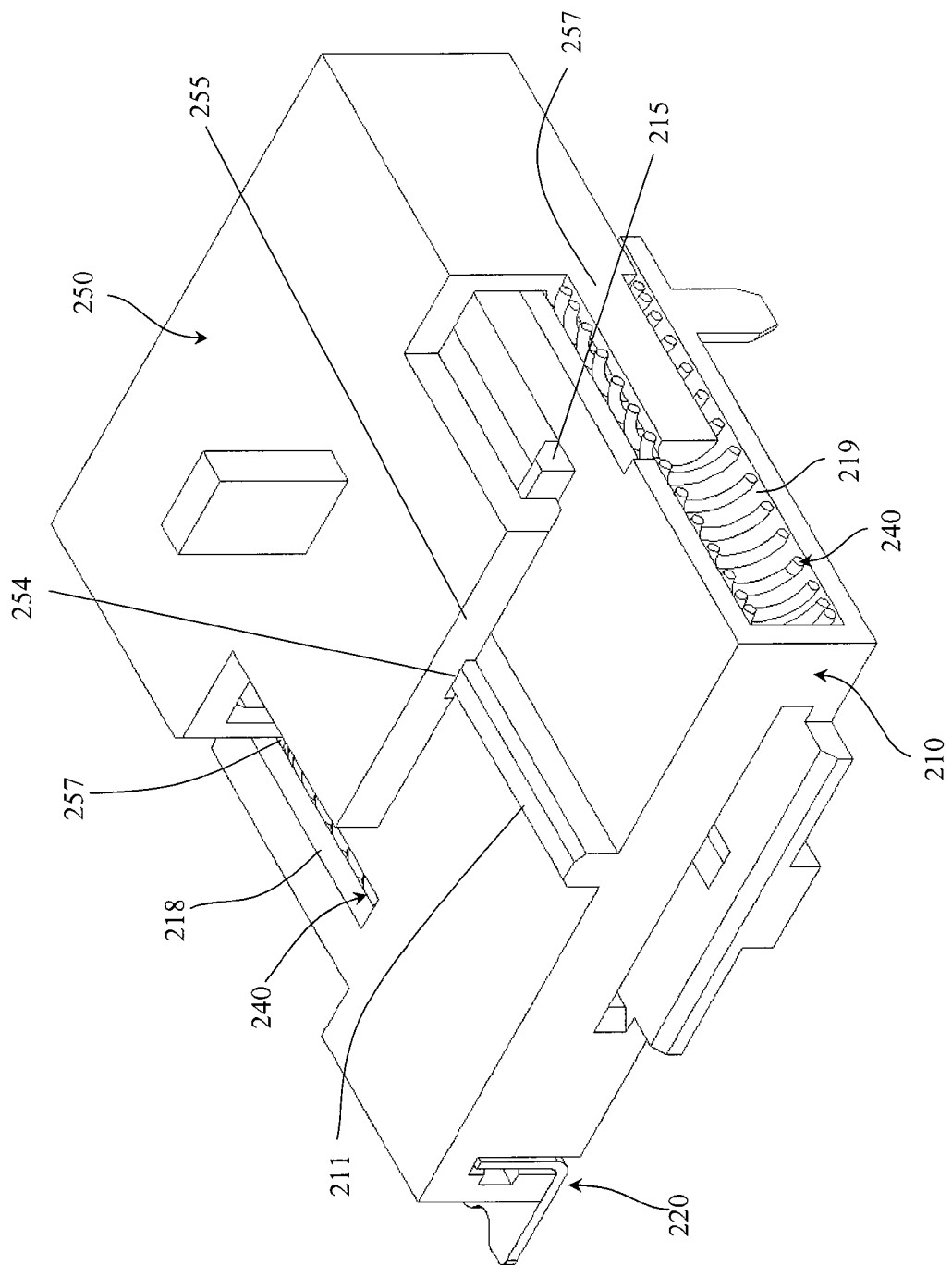
FIG. 6 illustrates a perspective view along another cross-sectional plane of a holding device in accordance with one embodiment of the present invention, wherein an elastic member is not compressed yet.

FIG. 6 illustrates a perspective view along another cross-sectional plane of the holding device 20, wherein an elastic member 240 is not compressed yet. As shown in FIG. 6, the first guiding track 218 and the second guiding track 219 are respectively located on the opposite sides of the holding device 20. The elastic members 240 are placed within the guiding tracks 218 and 219. Accordingly, the thrusting portion 257 of the ejection base 250 can move toward the elastic member 240 and also compress them smoothly and steadily along the passageways of the guiding track 218. The guiding tracks 218 and 219 provide a guiding path by which the ejection base 250 can move between the first placement (i.e. line a) and the second placement (i.e. line b). In addition, as aforementioned, the guiding portion 211 of the receiving casing 210 and the guiding groove 254 of the second portion 255 of the ejection base 250 also provides another guiding path for the movement of the ejection 250 between the first placement and the second placement. Accordingly, it should be understood that in the embodiment, there provides an ejection mechanism including the pusher 252 corresponding to the opening 213, the guiding groove 254 corresponding to the guiding portion 211, and the elastic member 240 together with the thrusting portion 257 corresponding to the guiding track 218/219. The holding device 20 with such ejection mechanism is used smoothly as it generates even stresses during operation.

The present invention has been described above with reference to preferred embodiments. However, those skilled in the art will understand that the scope of the present invention need not be limited to the disclosed preferred embodiments. On the contrary, it is intended to cover various modifications and equivalent arrangements within the scope defined in the following appended claims. The scope of the claims should be accorded the broadest interpretation so as to encompass all such modifications and equivalent arrangements.

What is claimed is:

1. A device for holding a medical test strip, the device comprising:

a receiving casing having an opening for receiving the medical test strip, a guiding portion, at least one guiding track and a first stopping portion protruding from an upper surface of the receiving casing;

an ejection base having a cover, at least one thrusting portion downwardly extended from the cover and a pusher beneath the cover, the cover downwardly extending a second stopping portion comprising a guiding groove for sliding against the upper surface of the receiving casing and selectively engaging with the first stopping portion, wherein the guiding groove movably engages with the guiding portion for leading the second stopping portion to slide against the upper surface of the receiving casing; and an elastic member located between the receiving casing and the ejection base, the elastic member comprising at least one spring placed in the guiding track, wherein an ejection mechanism comprising, the pusher corresponding to the opening, the guiding groove corresponding to the guiding portion, and the elastic member together with the thrusting portion corresponding to the guiding track, operates smoothly as the device generates less uneven stresses during operation;

wherein when the pusher moves toward the opening by an external force to eject the medical test strip from the opening, the elastic member is compressed and the second stopping portion slides away from the first stopping portion; and when the external force disappears, the second stopping portion slides toward the first stopping portion by a resilient force of the elastic member until the first stopping portion and the second stopping portion are engaged.

2. The device according to claim 1, wherein the first stopping portion and the second stopping portion are arranged in parallel with each other.

3. The device according to claim 1, wherein the first stopping portion is arranged perpendicular to the guiding portion.

4. The device according to claim 1, wherein:
the receiving casing further comprises two guiding tracks arranged on opposites of the receiving casing;
the elastic member comprises two springs respectively placed in the two guiding tracks; and
the ejection base further comprises two thrusting portions downwardly extended from the cover and respectively corresponding to the two guiding tracks,
wherein, when the pusher moves toward the opening, the two thrusting portions respectively enter the corresponding guiding track to compress the corresponding spring.

5. The device according to claim 1, wherein the spring is fitted into the guiding track.

6. The device according to claim 1, wherein:
the receiving casing further comprises an internal space and is profiled with a concave exposing a part of the internal space;
the medical test strip enters the internal space through the opening; and
the cover shelters the concave.

7. The device according to claim 4, wherein:
the receiving casing further comprises an internal space and is profiled with a concave exposing a part of the internal space;
the concave is between the two guiding tracks;
the medical test strip enters the internal space through the opening; and
the cover shelters the concave.

8. The device according to claim 1, further comprising at least one fastener having a vertical plane inserted into the receiving casing and a horizontal plane in connection with an external device.

9. The device according to claim 8, wherein in the fastener is L-shaped.

10. The device according to claim 8, further comprising two fasteners respectively inserted into opposite sides of the receiving casing, each fastener having a vertical plane inserted into the receiving casing and a horizontal plane in connection with an external member.

11. The device according to claim 1, wherein the pusher is formed with a stepping structure having a first step with a horizontal surface for supporting the medical test strip; the stepping structure further having a second step above the first step, the second step having a vertical surface to be against by an edge of the medical test strip.

12. The device according to claim 1, wherein the thrusting portion horizontally extending a linked shaft passing through the spring.

13. A device for holding a medical test strip, the device comprising:
a receiving casing having an opening for receiving the medical test strip, at least one guiding track, a first stopping portion and a guiding portion protruding from an upper surface of the receiving casing, the first stopping portion is arranged perpendicular to the guiding portion;
an ejection base having a cover and a pusher beneath the cover, at least one thrusting portion downwardly extended from the cover, the cover downwardly extending a second stopping portion arranged perpendicular to the guiding portion, the second stopping portion having a guiding groove movably engaged with the guiding portion so as to lead the second stopping portion to slide against the upper surface of the receiving casing, wherein the guiding groove movably engages with the guiding portion for leading the second stopping portion to slide against the upper surface of the receiving casing; and
an elastic member located between the receiving casing and the ejection base, the elastic member comprising at least one spring placed in the guiding track,
wherein an ejection mechanism comprising, the pusher corresponding to the opening, the guiding groove corresponding to the guiding portion, and the elastic member together with the thrusting portion corresponding to the guiding track, operates smoothly as the device generates less uneven stresses during operation;
wherein when the pusher moves toward the opening by an external force to eject the medical test strip from the opening, the elastic member is compressed and the second stopping portion slides away from the first stopping portion; and
when the external force disappears, the second stopping portion slides toward the first stopping portion by a resilient force of the elastic member until the first stopping portion and the second stopping portion are engaged.

* * * * *